US010939926B2

(12) United States Patent
Kam et al.

(10) Patent No.: US 10,939,926 B2
(45) Date of Patent: Mar. 9, 2021

(54) INDICATING POSITION AND LENGTH OF A BONE TUNNEL AND IMPLEMENTATIONS THEREOF

(71) Applicant: Conmed Corporation, Utica, NY (US)

(72) Inventors: Andrew Kam, Odessa, FL (US); Brenda Yantzer, Temple Terrace, FL (US); Joshua Dines, Southampton, NY (US); Orr Limpisvasti, Manhattan Beach, CA (US); Thay Lee, Long Beach, CA (US)

(73) Assignee: Conmed Corporation, Utica, NY (US)

( * ) Notice: Subject to any disclaimer, the term of this patent is extended or adjusted under 35 U.S.C. 154(b) by 818 days.

(21) Appl. No.: 15/075,731

(22) Filed: Mar. 21, 2016

(65) Prior Publication Data

US 2016/0270801 A1   Sep. 22, 2016

Related U.S. Application Data

(60) Provisional application No. 62/136,560, filed on Mar. 22, 2015.

(51) Int. Cl.
*A61B 17/17* (2006.01)
*A61B 90/00* (2016.01)
*A61B 17/00* (2006.01)

(52) U.S. Cl.
CPC .......... *A61B 17/1714* (2013.01); *A61B 90/06* (2016.02); *A61B 2017/0046* (2013.01); *A61B 2090/061* (2016.02); *A61B 2090/062* (2016.02)

(58) Field of Classification Search
CPC ............ A61B 17/1714; A61B 17/1717; A61B 17/1764; A61B 2090/061; A61B 2090/062; A61B 2017/0046
See application file for complete search history.

(56) References Cited

U.S. PATENT DOCUMENTS

| 4,787,377 | A | * | 11/1988 | Laboureau | ......... | A61B 17/1714 606/84 |
| 5,573,538 | A | * | 11/1996 | Laboureau | ......... | A61B 17/1714 606/86 R |
| 5,681,320 | A | * | 10/1997 | McGuire | ............ | A61B 17/0401 606/104 |
| 5,688,284 | A | * | 11/1997 | Chervitz | ............ | A61B 17/1714 606/102 |
| 5,891,150 | A | * | 4/1999 | Chan | .................. | A61B 17/1714 606/96 |

(Continued)

FOREIGN PATENT DOCUMENTS

EP        2561815       2/2013

OTHER PUBLICATIONS

International Search Report Form PCT/ISA/220, International Application No. PCT/US2016/023402, pp. 1-10, dated Jun. 6, 2016.

*Primary Examiner* — Matthew J Lawson
(74) *Attorney, Agent, or Firm* — Bond, Schoeneck & King, PLLC; Frederick J. M. Price (57) ABSTRACT

An apparatus for indicating the position and length of a bone tunnel, including a first member configured to couple with a drill guide; and a second member in spaced relation to the first member, the second member comprising an indicator configured to provide an indication of thickness of a boney member with the first member disposed on a first side of the boney member and the second member disposed on a second side of the boney member.

14 Claims, 11 Drawing Sheets

(56) References Cited

U.S. PATENT DOCUMENTS

| | | | |
|---|---|---|---|
| 8,986,316 B1* | 3/2015 | Jordan | A61B 17/1714 606/96 |
| 10,123,812 B1* | 11/2018 | Alvarado | A61B 17/1764 |
| 10,219,813 B2* | 3/2019 | Okuno | A61B 17/1714 |
| 2006/0069394 A1* | 3/2006 | Weiler | A61B 17/1714 606/96 |
| 2007/0205567 A1* | 9/2007 | Eberle | A61B 17/00 279/77 |
| 2008/0103506 A1* | 5/2008 | Volpi | A61B 17/1714 606/96 |
| 2008/0157488 A1* | 7/2008 | Kullmer | A61B 17/00 279/76 |
| 2010/0324556 A1* | 12/2010 | Tyber | A61B 17/1717 606/62 |
| 2011/0034933 A1* | 2/2011 | Paulos | A61B 17/1714 606/88 |
| 2012/0059382 A1* | 3/2012 | Paulos | A61B 17/1714 606/96 |
| 2012/0197259 A1* | 8/2012 | Smith | A61B 17/1714 606/88 |
| 2013/0030442 A1* | 1/2013 | Pilgeram | A61B 17/1714 606/96 |
| 2013/0030446 A1* | 1/2013 | Wayne | A61B 17/1717 606/104 |
| 2013/0053959 A1* | 2/2013 | Lizardi | A61B 17/1714 623/13.14 |
| 2016/0089159 A1* | 3/2016 | Ardito | A61B 17/1714 606/96 |
| 2016/0302805 A1* | 10/2016 | Meridew | A61B 17/1714 |

* cited by examiner

INDICATING POSITION AND LENGTH OF A BONE TUNNEL AND IMPLEMENTATIONS THEREOF

CROSS-REFERENCE TO RELATED APPLICATIONS

The present application claims priority to and the benefit of U.S. provisional patent application No. 62/136,560, filed on Mar. 22, 2015, the entire contents of which are hereby incorporated by reference.

BACKGROUND OF THE INVENTION

1. Field of the Invention

The present disclosure is directed generally to surgical devices and surgical procedures for drilling into a bone, and more particularly, to a surgical device for indicating the position and length of a bone tunnel prior to penetrating the bone.

2. Description of the Related Art

Many surgical procedures to repair torn or damaged tissue require the surgeon to form a tunnel in a bone or boney member. The tunnel serves as a site to anchor repair tissue or sutures. For reconstructive repair of the knee, for example, tunnels penetrate through both the tibia and femur to allow graft tissue to extend all the way through these bones. The graft tissue operates to join the bones together to restore normal functions of the joint. The positioning of the bone tunnel is considered to be one of the most important factors determining the success of a knee reconstruction. It is important, therefore, that the tunnels are in the proper position and of sufficient length to ensure the most secure attachment of the repair tissue. This ability to precisely identify the location and trajectory of the potential bone tunnel is made more difficult when using a guide with a bent or curved tip.

As the positioning of the bone tunnel is directly influenced by the surgeon, it is critical that a device used by the surgeon to execute the bone tunnel be precise and easy to use intraoperatively. Drill guides are known in the art for facilitating the formation of a bone tunnel; however, these guides lack a feature for providing measurements of the bone tunnel length. The ability to measure the length of a potential bone tunnel could provide the surgeon with more information to determine where to place the bone tunnel.

Accordingly, there is a need in the art for a surgical tool to facilitate the drilling of a bone tunnel with a feature for providing measurements of the bone tunnel length.

Description of the Related Art Section Disclaimer: To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional devices for determining the position of a bone tunnel as described above. Therefore, a need exists for a simple to use device which engages opposing sides of a boney member to indicate location of potential bone tunnel apertures and measure the length of a potential bone tunnel. Various embodiments of the present invention may be advantageous in that they may solve or reduce one or more of the potential problems and/or disadvantages discussed herein.

The present disclosure is directed to an inventive configuration, structure, and resulting function of an apparatus for providing an indication of position and length of a bone tunnel prior to penetrating the bone. Various embodiments herein are directed to an apparatus for indicating the position and length of a bone tunnel, including, but not limited to: a first member configured to couple with a drill guide; and a second member in spaced relation to the first member, the second member comprising an indicator configured to provide an indication of thickness of a boney member with the first member disposed on a first side of the boney member and the second member disposed on a second side of the boney member.

According to an alternative embodiment, the apparatus for indicating the position and length of a bone tunnel, includes, but is not limited to a shaft having a bent portion; a first member coupled with the shaft, the first member comprising a body with a first axis and configured to couple with a drill guide; and a second member coupled with the shaft, the second member having a second axis, wherein the shaft is configured to locate the second member in spaced relation to the first member so that the second axis aligns with a drill axis at an end of the drill guide.

According to an another aspect, a system for use with a drill guide to measure a length of a tunnel in a bone includes, but is not limited to, a support structure with a first axis and a second axis intersecting at a drill angle; and a transitory member configured to move relative to the support structure, the bone, the transitory member comprising a gauge marker, wherein, with the support structure in position on the drill guide, the drill angle is configured to align the second axis with a drill axis at a curved end of the drill guide, and wherein the gauge marker has a first position and a second position relative to the support structure, at least one of which corresponds with a value for the length for the tunnel that is zero.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

Figure 1:
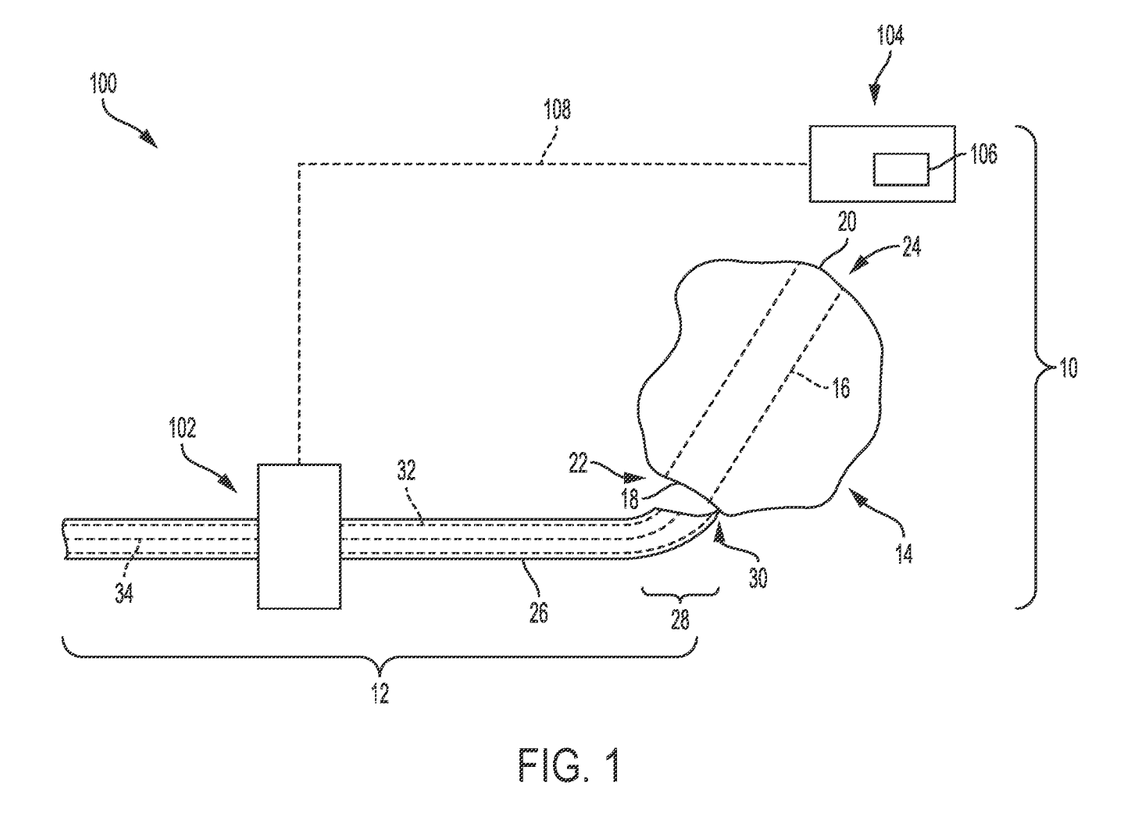
FIG. 1 is a perspective view schematic representation of an exemplary embodiment of an apparatus to provide an indication of a length of a potential tunnel in a bone in accordance with an embodiment.

Referring now to the drawings, wherein like reference numerals refer to like parts throughout, there is seen in FIG. 1 a perspective view schematic representation of an exemplary embodiment of an apparatus 100 to locate a tunnel prior to drilling. The apparatus 100 is part of a system 10 that can include a drill guide 12 and drill (not shown). The system 10 is shown proximate a boney member 14. In use, the system 10 can locate a potential tunnel 16 of length L in a boney member 14. The tunnel 16 can have an entrance 18 and an exit 20 wherein the entrance 18 is disposed on a first side 22 of the boney member 14 and the exit 20 is disposed on an opposing second side 24 of the boney member 14.

As also shown in FIG. 1, the drill guide 12 has an elongated structure 26 terminating at bent or curved end 28 with a tip 30 designed to direct a flexible guide pin at an angled trajectory to create a longer bone tunnel. The elongated structure 26 is cannulated, forming a bore 32 with a drill axis 34. During a surgical procedure and prior to drilling, the surgeon can position the tip 30 in a location on the first side 22 against the boney member 14. The tip 30 engages the boney member 14 to maintain the position of the system 10. Specifically, the tip 30 operates as a fulcrum wherein the surgeon can move the system 10 in position relative to the boney member 14.

The apparatus is configured as an aid to locate the potential tunnel 16 prior to any breach of the boney member 14. This aid provides an indication of the thickness of the boney member 14 at the exit 20 measured between the sides 22, 24. The thickness corresponds with length L of the potential tunnel 16 in many surgical procedures in which the potential tunnel 16 penetrates through the boney member 14 (as shown in FIG. 1). In response to movement of the system 10 by the surgeon, the indication on the apparatus 100 changes to reflect the thickness at various points along the surface of the second side 24 of the boney member 14. Thus, the surgeon is provided with an easily visible and immediate indication that the thickness of the boney member 14 has changed. This feature avoids unnecessary trauma to the boney member 14. For example, the surgeon can use the apparatus 100 to select the position for the potential tunnel 16 that is best situated to receive and secure tissue (or other material) in the boney member 14 prior to drilling. Then, with the drill guide 12 in the appropriate position, the surgeon can proceed to form the potential tunnel 16, typically by first inserting the flexible guide pin (not shown) through the bore 32 of the drill guide 12 to puncture the boney member 14. The surgeon can then locate a separate, flexible guide pin on the second side 24 of the boney member 14. The flexible guide pin can be used with the drill and a drill bit (not shown) that inserts over the flexible guide pin and is sized to create the potential tunnel 16 with an appropriate diameter, as desired.

Referring again to FIG. 1, the apparatus 100 can have a support structure with a first member 102 (as "fastening member 102") and a second member 104 (also, "gauge member 104"). The members 102, 104 are disposed on opposite sides 22, 24 of the boney member 14. These positions are useful to present the indication (at the gauge member 104) in a manner that is visible to the surgeon and surgical staff during the procedure. In one example, the fastening member 102 is configured to couple with the drill guide 12. Upon fastening, the gauge member 104 is maintained coplanar with the bore 32 of the drill guide 12. The gauge member 104 can be configured with an indicator 106 to provide the indication of material thickness and, in turn, the length L of the potential tunnel 16. In one embodiment, the support structure can also include a coupling member, generally indicated by the dashed line enumerated as 108. The coupling member 108 can provide structure (e.g., frame members) to couple the members 102, 104 together in a spaced relationship. In the system 10, this spaced relationship locates the fastening member 102 and the gauge member 104 on the first side 22 and the second side 24 of the boney member 14 (as shown in FIG. 1), respectively.

Figure 2:
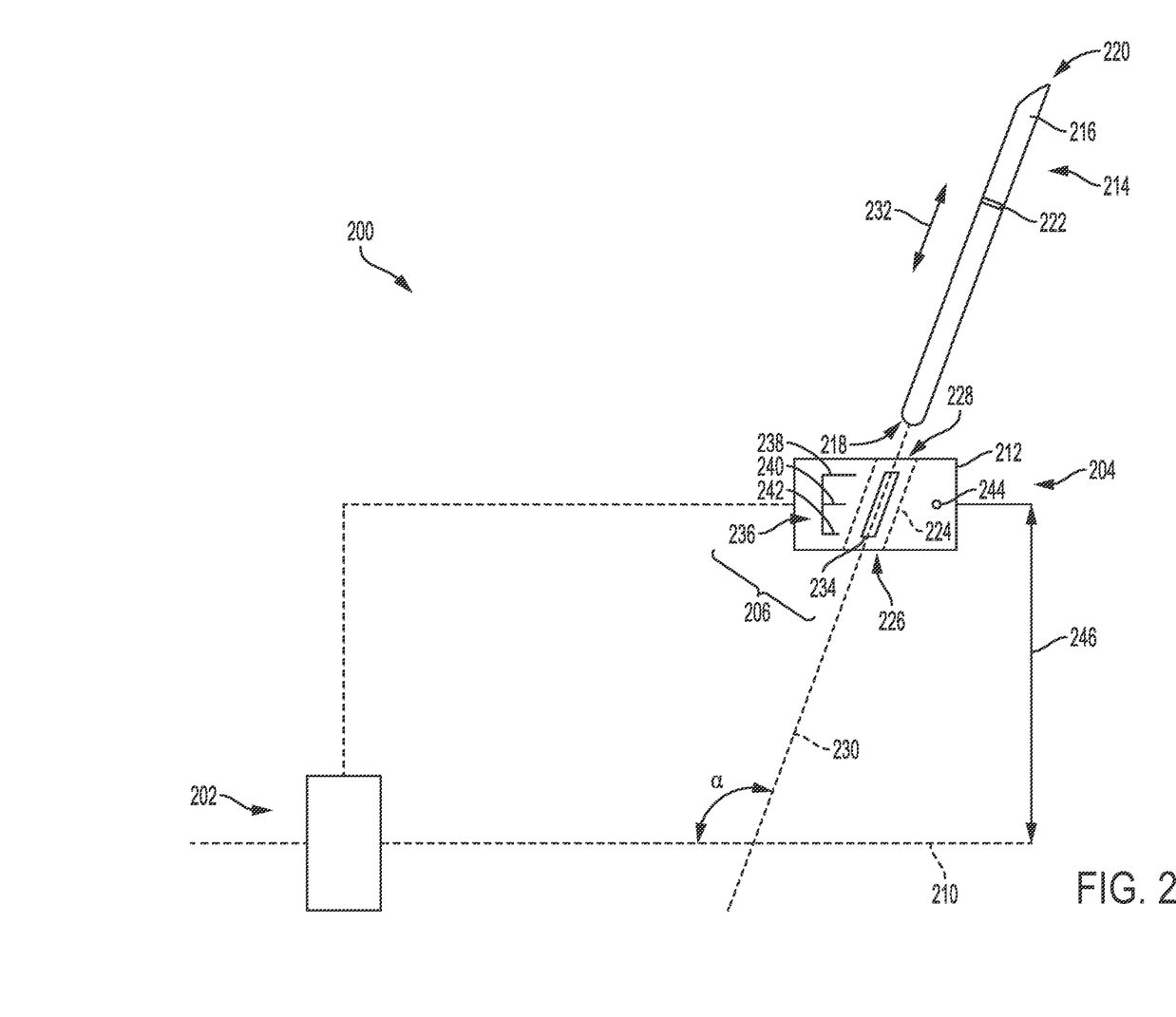
FIG. 2 is a perspective view schematic representation of an exemplary embodiment of an apparatus to provide an indication of a length of potential tunnel in a bone in accordance with an embodiment.

Referring now to FIG. 2, there is shown a perspective view schematic representation of an apparatus 200 in partially exploded form. The fastening member 202 defines a first axis 210. The gauge member 204 includes a guide member 212 and a transitory member 214, preferably an elongated body 216 with a pair of ends (e.g., a distal end 218 and a proximal end 220). The elongated body 216 can also include a gauge maker 222 spaced longitudinally apart from the ends 218, 220. As also shown in FIG. 2, the guide member 212 has a bore 224 with a pair of open ends (e.g., a first end 226 and a second end 228) and a second axis 230 extending therebetween. The bore 224 is oriented so that the second axis 230 intersects the first axis 210 at a guide angle α. Values for the guide angle α are nominally in a range of from approximately 90 degrees to approximately 180 degrees and, in one example, the guide angle α is approximately 140 degrees. In one implementation, the value for the guide angle α aligns the second axis 230 with the drill axis 34 (FIG. 1) at the curved end 28 of the drill guide 12 (FIG. 1). This alignment is useful to position the elongated body 216 along the travel of the guide wire and drill bit into the boney member 14. In this way, the apparatus 200 can provide the surgeon with a visual approximation for the exit 20 (FIG. 1) of the potential tunnel 16 (FIG. 1) from the boney member 14 (FIG. 1).

The bore 224 is configured to receive the distal end 218 of the elongated body 216. This configuration aligns the elongated body 216 with the second axis 230. In use, the elongated body 216 can move relative to the guide member 212 along the second axis 230, as indicated by the arrow enumerated 232. Movement 232 changes the position of the gauge marker 222 from a first position to a second position. To facilitate the movement 232, the apparatus 200 may utilize a loose slip fit between the dimensions of the interior surface of the bore 224 and the dimensions of the outer surface of the elongated body 216. In some embodiments, it may be preferred to use a slight interference fit to retain the elongated body 216 in position relative to the guide member 212 until acted on, e.g., by the surgeon during the surgical procedure.

Referring again to FIG. 2, the indicator 206 is configured to provide a visual representation of the indication of material thickness (and length L of the potential tunnel 16 of FIG. 1). The indicator 206 can include an aperture 234 and a gauge 236. The aperture 234 penetrates the guide member 212. This feature may embody an elongated slot to expose a portion of the bore 224; however, this disclosure does contemplate that other geometry, e.g., one or more annular and/or circular openings, might also provide geometry that is suitable for use in the embodiment.

The gauge 236 has one or more markings (e.g., a first marking 238, a second marking 240, and a third marking 242) that reside proximate the aperture 234. The markings 238, 240, 242 relate to a reference point, shown generally as point 244. The reference point 244 is useful to solidify a position of the gauge 236 on the guide member 212 and on the apparatus 200, generally. This position ensures the location of the gauge marker 222 relative to the markings 238, 240, 242, and reflects the material thickness of the boney member 14 (FIG. 1). In one example, the location of the reference point 244 is defined by one or more coordinates (e.g., a first or radial coordinate 246). The radial coordinate 246 measures a distance between the reference point 244 and the first axis 210. As discussed more below, this distance accommodates for the offset between the first axis 210 and the tip 30 (FIG. 1) of the drill guide 12 (FIG. 1).

Figure 3:
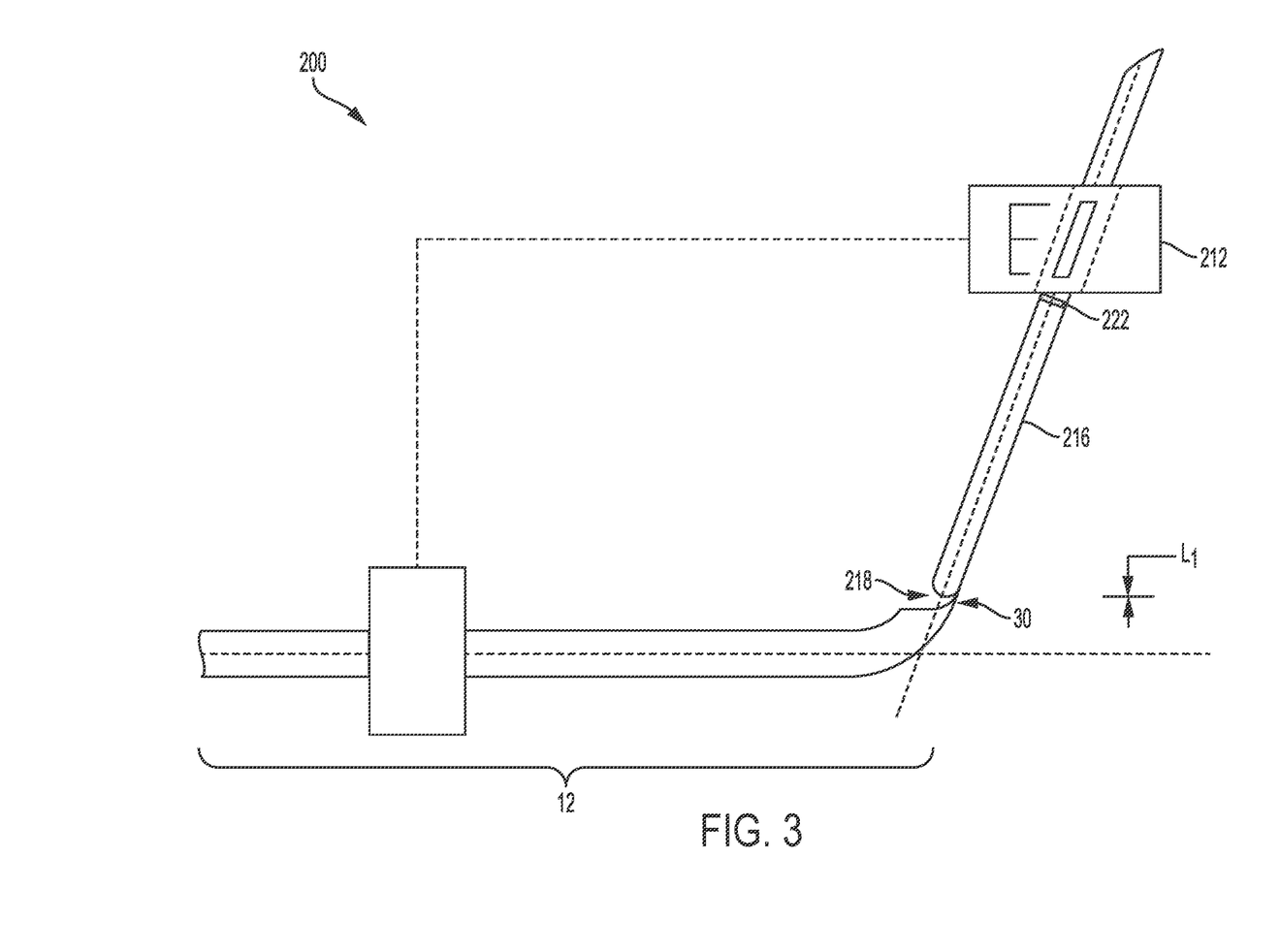
FIG. 3 is a perspective view schematic representation of the apparatus of FIG. 2 with parts positioned to provide an indication of a first length in accordance with an embodiment.
Figure 4:
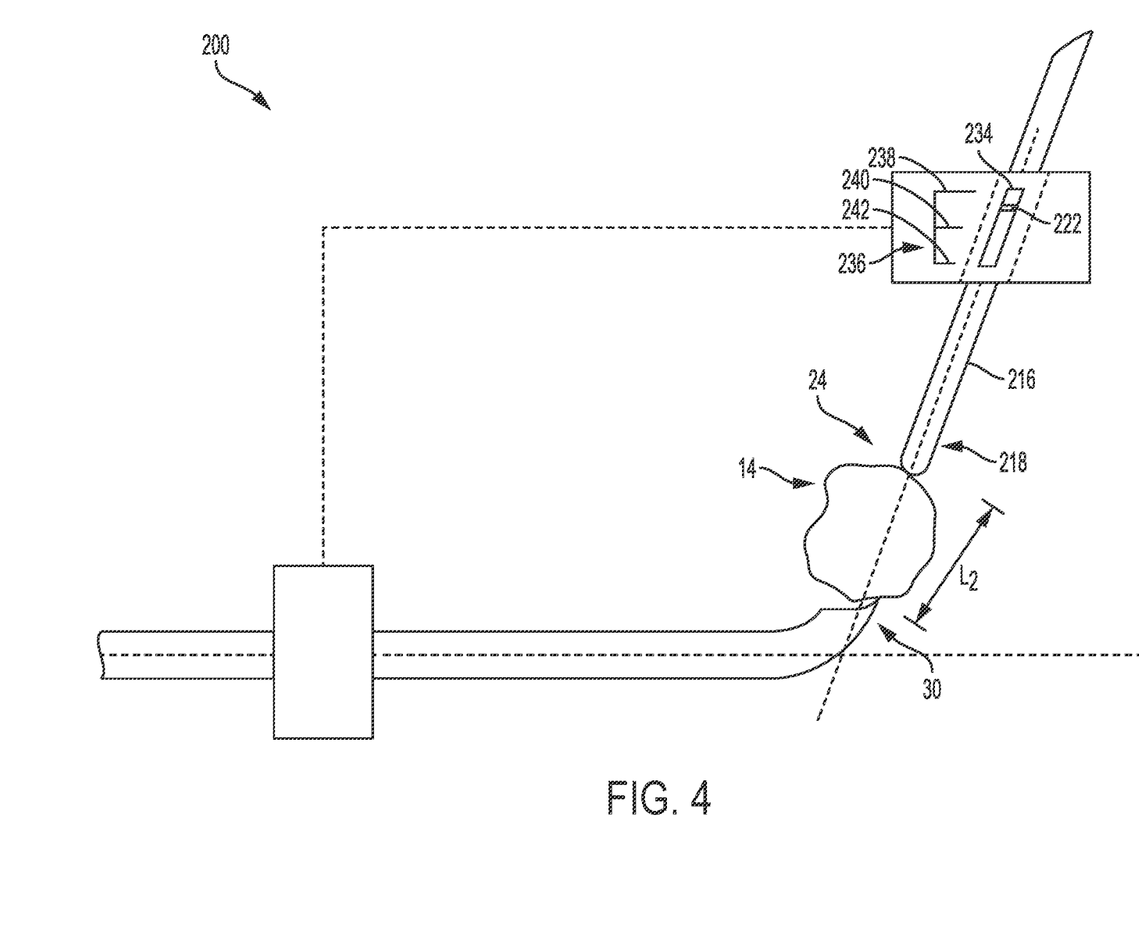
FIG. 4 is a perspective view schematic representation of the apparatus of FIG. 2 with parts positioned to provide an indication of a second length in accordance with an embodiment.

Referring now to FIGS. 3 and 4, there are shown perspective view schematic representations of the apparatus of FIG. 2 with parts positioned to provide an indication of a first length and a second length, respectively. FIG. 3 illustrates an example of the apparatus 200 in assembled form with the gauge marker 222 in the first or zero position, and FIG. 4 illustrates an example of the apparatus 200 in assembled form with the gauge marker 222 in the second or measured position. In FIG. 3, the apparatus 200 is configured with the distal end 218 of the elongated body 216 disposed proximate the tip 30 of the drill guide 12. The gauge marker 222 is located on the elongated body 216 so that the zero position corresponds with a length L1 that is approximately zero (or null). In one implementation, the apparatus 200 may be configured for the gauge marker 222 to reside outside of the guide member 212 in the zero position as shown in FIG. 3. This zero position is useful for the surgeon or surgical staff to calibrate the apparatus 200 (e.g., to ensure that the elongated body 216 is properly selected with respect to the drill guide 12 prior to use during the surgical procedure). FIG. 4 shows the apparatus 200 with the distal end 218 of the elongated body 216 in contact with the second side 24 of the boney member 14. The gauge marker 222 is found within the aperture 234 and proximate the gauge 236. The gauge 236 is configured to approximate the length L2 so that, in use, the surgeon can estimate the length L2 in accordance with the relationship between the gauge marker 222 and the gauge markings 238, 242, 244.

Figure 5:
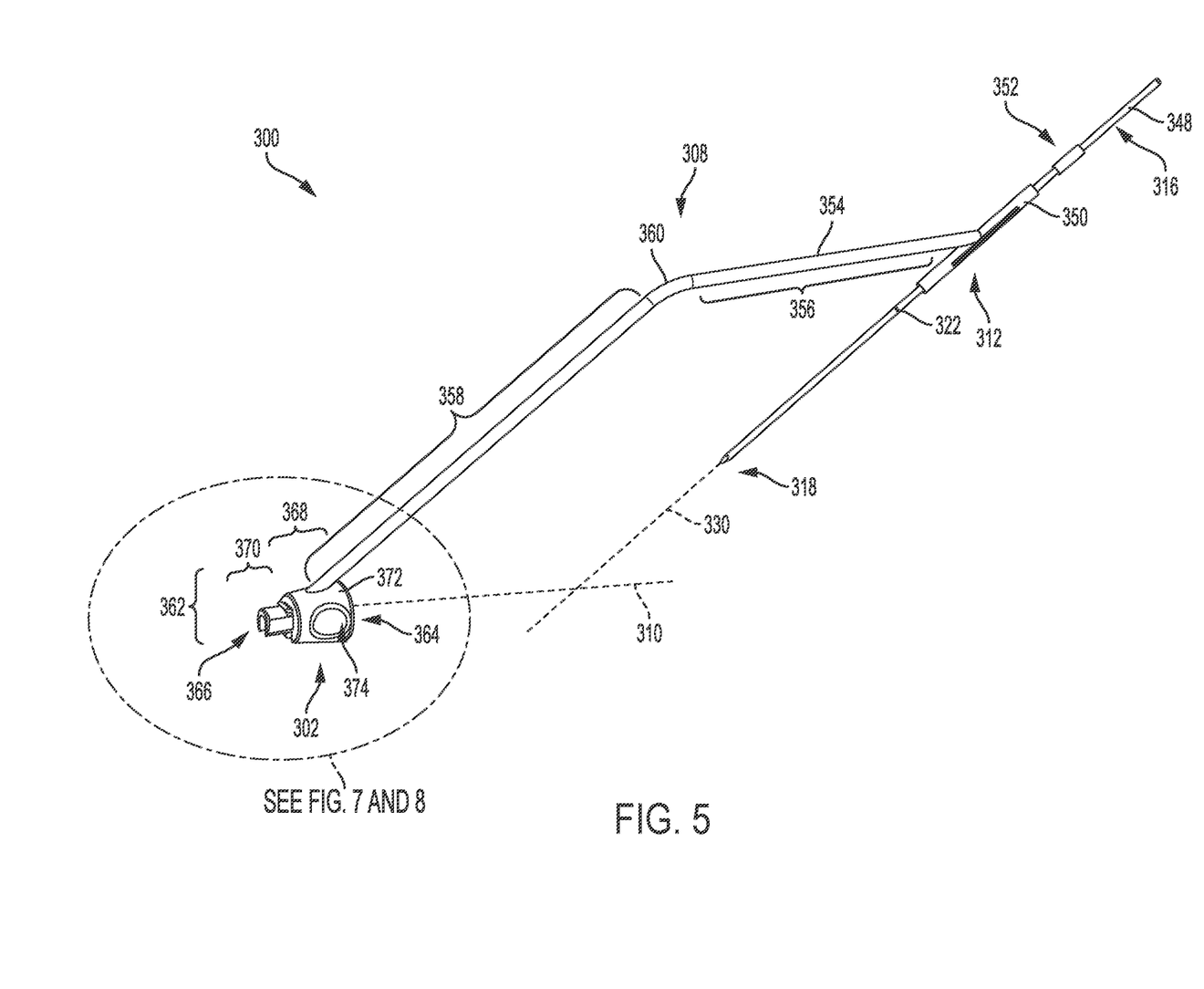
FIG. 5 is a perspective view schematic representation of an exemplary embodiment of an apparatus to provide an indication of a length of a potential tunnel in a bone in accordance with an embodiment.

Referring now to FIG. 5, there is shown a perspective view schematic representation of an exemplary embodiment of an apparatus 300 in assembled form. Moving from right to left in the diagram, the elongated body 316 embodies a pin 348 of generally cylindrical cross-section. The guide member 312 can embody a tube 350 or like thin-walled cylinder that is configured to receive the pin 348. The tube 350 may lend itself to constructions of sheet metal that is bent or formed around the second axis 330, although the part may be machined from a block or billet of material.

The pin 348 may be constructed of metal (e.g., stainless steel) or other suitable surgical material, typically as turned and/or extruded shaft. At the distal end 318, the shaft can terminate at a sharp point, or tapered end, that is configured to pierce skin and/or bone, as necessary. The gauge marker 322 can be formed on the metal shaft using etching and related techniques (e.g., paint, dye, plating, etc.). In on example, the pin 348 can include an identifier 352 to allow the surgeon or surgical staff to visually identify the pin 348. The identifier 352 may indicate the type and/or style of the pin 348, and/or may show that the pin 348 is useful for and/or corresponds with a particular surgical procedure or application.

The coupling member 308 can include a shaft 354. The shaft 354 can be solid or hollow, in whole or in part. Selected construction may depend at least in part on weight and cost considerations for the apparatus 300. The construction will preferably use surgical grade metals and like material of sufficient strength, rigidity, and durability. It is important, for example, that the construction can maintain the spaced relationship between the fastening member 302 and the tube 350 after repeated usage as necessary within the disclosed subject matter contemplated herein.

Figure 10:
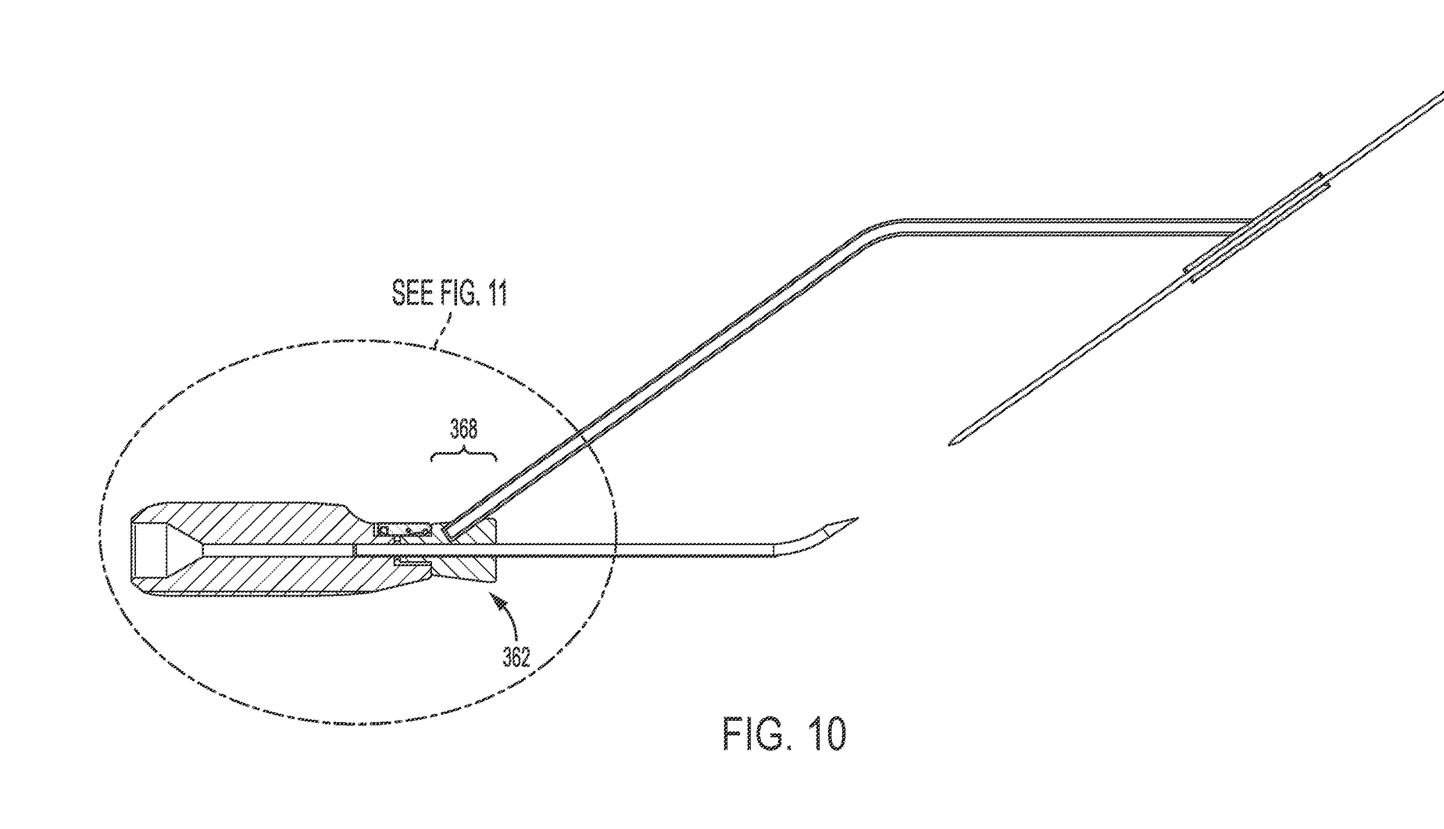
FIG. 10 is an elevation view of the cross-section of the apparatus of FIG. 9 in accordance with an embodiment.
Figure 11:
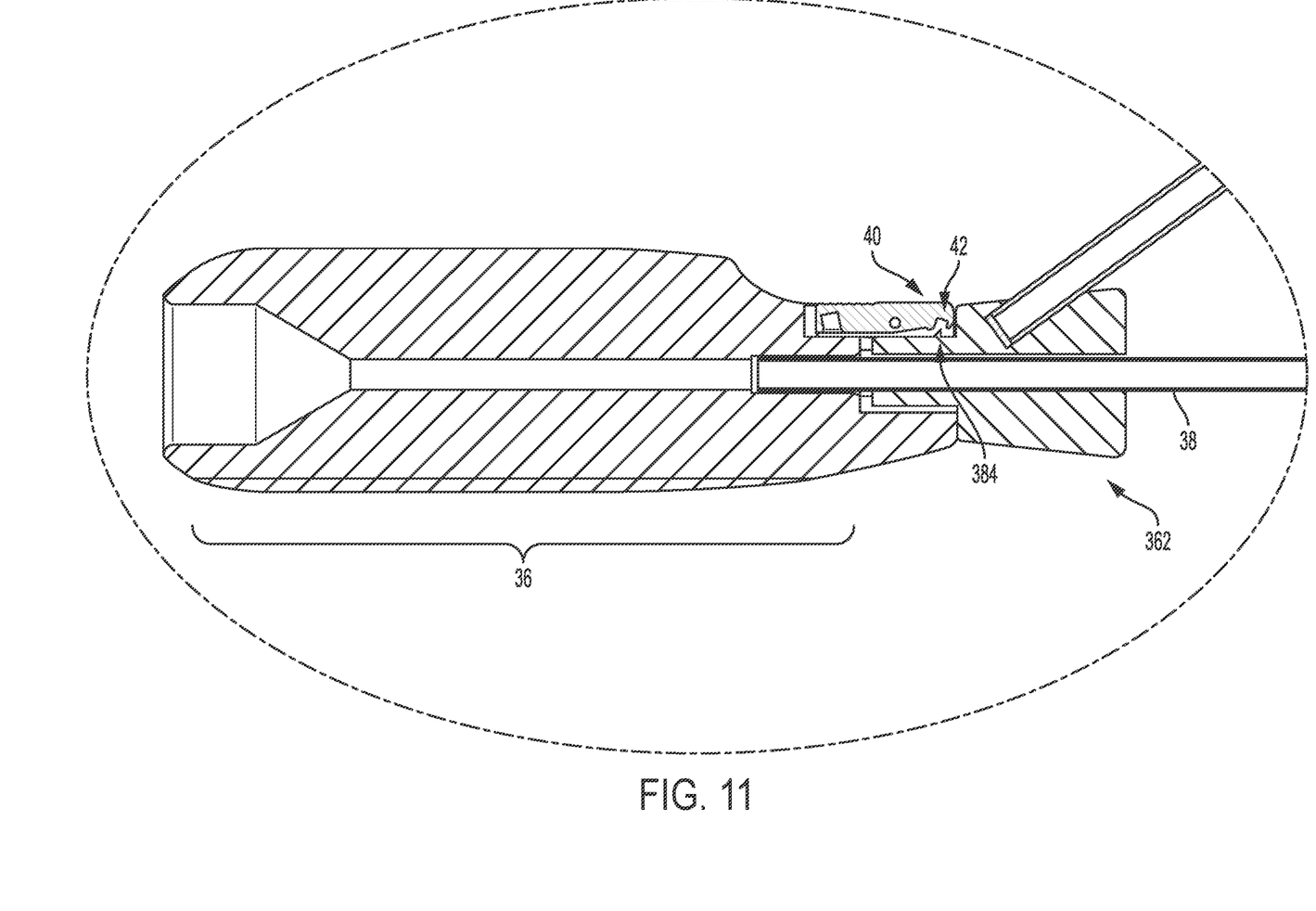
FIG. 11 depicts a detail of the apparatus of FIG. 10 in accordance with an embodiment.

The shaft 354 can have one or more generally straight portions (e.g., a first portion 356 and a second portion 358) and a bent portion 360 disposed therebetween. On one end of the shaft 354, the first portion 356 couples with the tube 350, preferably using a weld and/or similar fastening technique, although these components may be configured for fasteners (e.g., screws). In one example, the apparatus 300 may include one or more intermediary pieces (e.g., a clamp and/or a bracket) to secure the first portion 356 and the tube 350 together. At the other end of the shaft 354, the second portion 358 couples with the fastening member 302. The second portion 358 may penetrate into the fastening member 302 (as shown in FIGS. 10 and 11 below).

The fastening member 302 has a body 362 with a first end 364 and a second end 366. The features of the body 362 may lend to machining, casting, or molding of suitable materials (e.g., metals, plastics, composites, etc.). In one implementation, the body 362 is configured into at least a pair of sections (e.g., a first section 364 and a second section 366). In the first section 364, the body 362 has an outer surface 372 that tapers inwardly towards the first axis 310 from the first end 364 towards the second end 366. The taper forms the body 362 with a generally frusto-conical shape. The outer surface 372 also can have one or more depressions (e.g., a first depression 374). These depressions can populate the body 362 to facilitate implementation of fastening member 302 on the drill guide 12 (FIGS. 1, 3, and 4). For example, the depressions can be configured to receive or more fingers (e.g., thumb and forefinger) of the surgeon, thus improving tactile feel and increasing leverage for the surgeon to engage the fastening member 302 onto the drill guide (FIGS. 1, 3, and 4).

Figure 6:
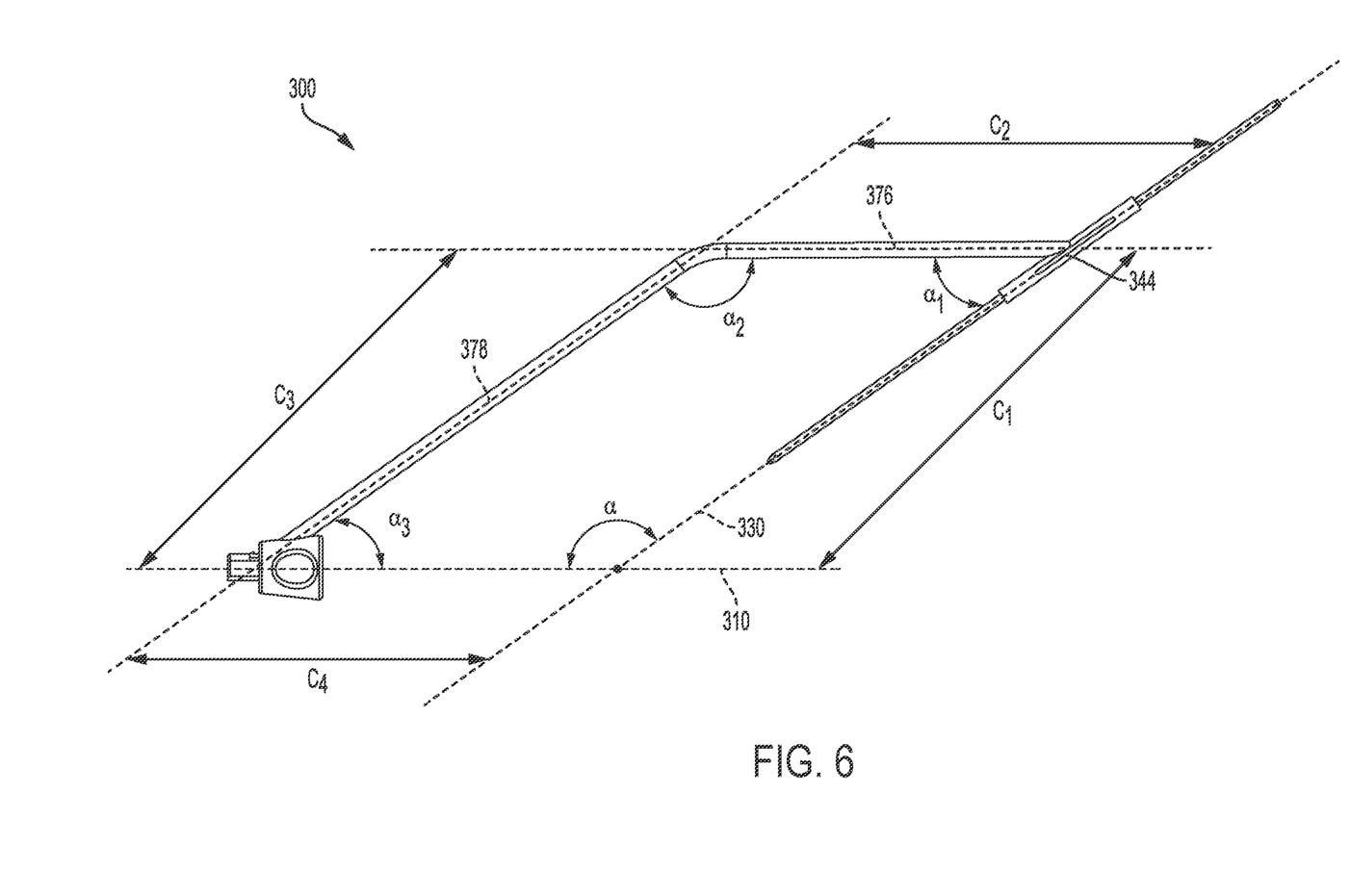
FIG. 6 is an elevation view of the apparatus of FIG. 5 in accordance with an embodiment.

FIG. 6 depicts an elevation view of the apparatus 300. The structure of the apparatus 300 has a profile that is useful to locate the reference point 344 and, thus, coordinate dimensions for the gauge marker 222 (FIGS. 2, 3, and 4), the gauge 236 (FIGS. 2, 3, and 4), and the gauge markings 238, 240, 242 (FIGS. 2, 3, and 4) as contemplated herein. The profile includes the first axis 310 and the second axis 330. The profile also includes a third axis 376 and a fourth axis 378, one each formed by the first portion 356 and the second portion 358 of the shaft 354, respectively. As shown in FIG. 6, in the profile, the third axis 376 intersects with the second axis 330 at an angle $\alpha 1$ and with the fourth axis 378 at $\alpha 2$. Proximate the fastening member 302, the fourth axis 378 intersects the first axis 310 at an angle $\alpha 3$. In one implementation, the profile for the structure of the apparatus 300 is configured in accordance with Equations (1), (2), (3), and (4) below:

$$C_1 = C_3, \quad \text{Equation (1)}$$

$$C_2 = C_4, \quad \text{Equation (2)}$$

$$\alpha = \alpha_2, \quad \text{Equation (3)}$$

$$\alpha_1 = \alpha_3, \quad \text{Equation (4)}$$

wherein C1 measures the length between the first axis 310 and the third axis 376 (along the second axis 330), C2 measures the length between the second axis 330 and the fourth axis 378 (along the third axis 376), C3 measures the length between the first axis 310 and the third axis 376 (along the fourth axis 378), and C4 measures the length between the second axis 330 and the fourth axis 378 (along the first axis 310).

Figure 7:
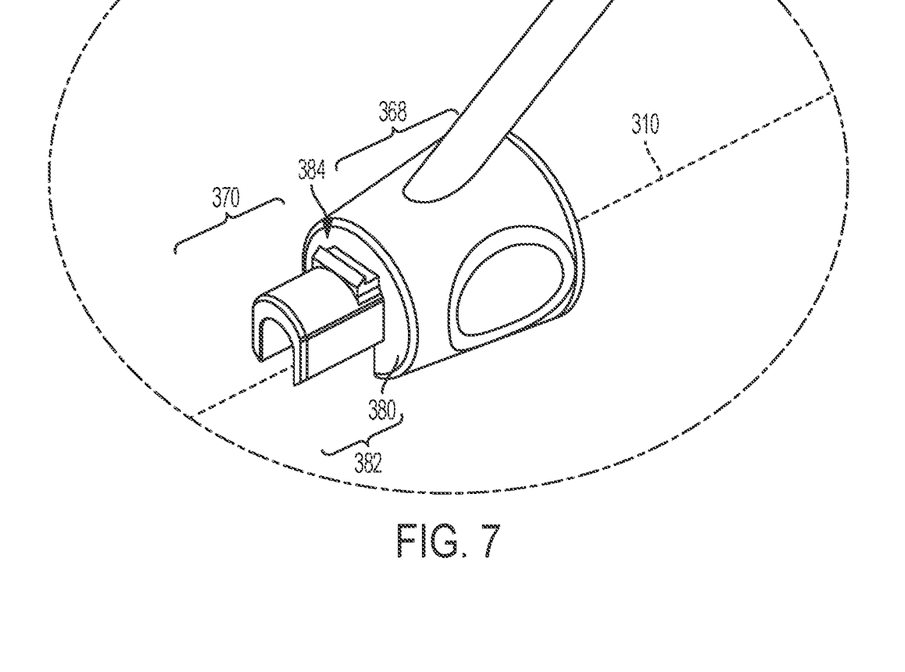
FIG. 7 is a detail view of the apparatus of FIG. 5 in accordance with an embodiment.

Referring now to FIG. 7, there is shown a detail view of the apparatus in FIG. 5. The body 362 has a planar surface 380 arranged perpendicular to the first axis 310. The planar surface 380 can serve as a reference, separating the sections 368, 370. In the second section 370, the body 362 has a reduced diameter (as compared to the diameter of the body 362 in the first section) with an elongated protrusion 382 that extends along the first axis 310 and away from the planar surface 380. The elongated protrusion 382 supports a hasp element 384. Configurations of the hasp element 384 can embody a hook, clip, or like fastener. In use, this fastener is configured to releasably engage the body 362 with the drill guide 12 (FIG. 1) as noted herein.

Figure 8:
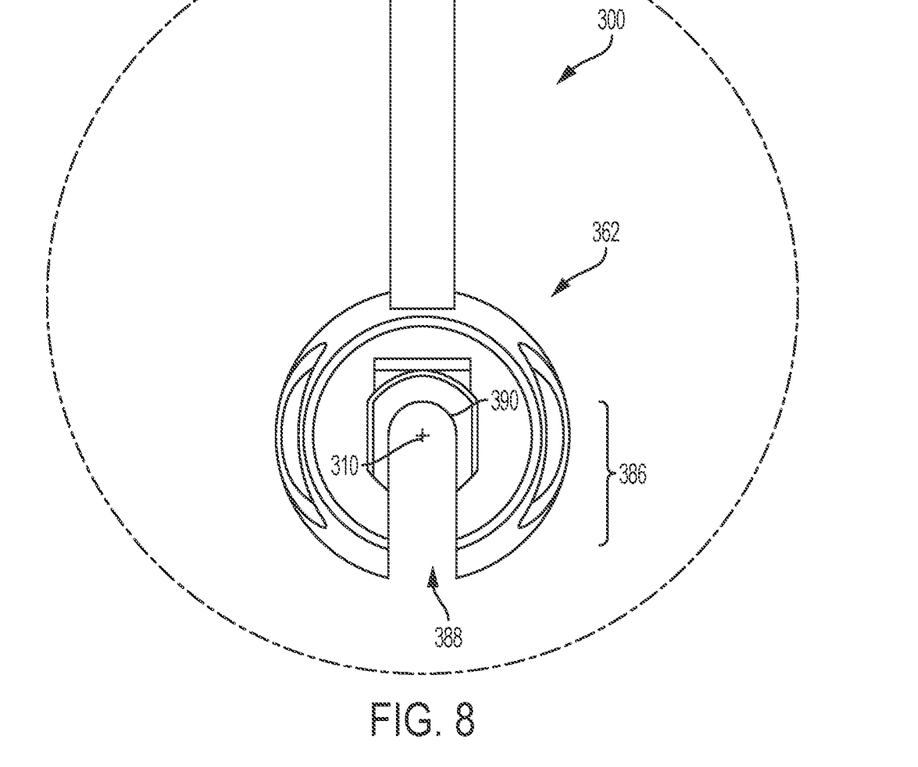
FIG. 8 is a detail view of the apparatus of FIG. 5 in accordance with an embodiment.

Referring now to FIG. 8, there is shown an elevation view of the back of the apparatus 300 of FIG. 7. The body 362 includes a slotted bore 386 with an open bottom portion 388 and annular top portion 390. The slotted bore 386 penetrates through the body 362 along the first axis 310. The annular top portion 390 circumscribes the first axis 310. In one implementation, the diameter of the annular top portion 390 and width of the open bottom portion 377 are configured to receive the elongated structure 26 (FIG. 1) of the drill guide 12 (FIG. 1) therein. This configuration allows the surgeon to rest the body 362 on the elongated structure 26 (FIG. 1) and insert the body 362 into a portion of the drill guide 12 (FIG. 1). The hasp element 388 will retain the body 362 in the inserted position.

Figure 9:
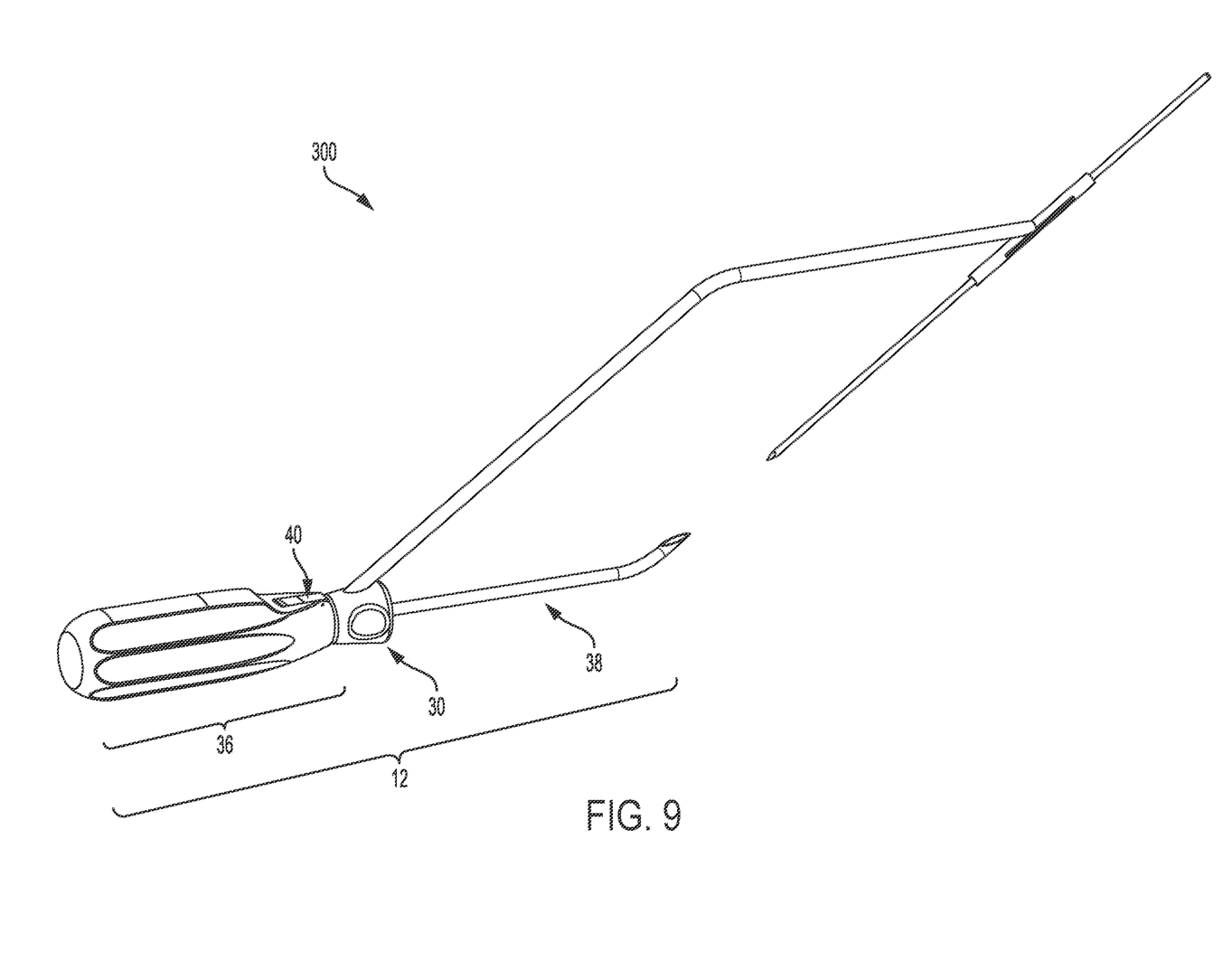
FIG. 9 is a perspective view of the apparatus of FIGS. 5, 6, 7, and 8 disposed on an example of a drill guide in accordance with an embodiment.

Referring now to FIGS. 9-11, there are shown various views of the apparatus 300 in position on an exemplary drill guide 12. FIG. 9 is a perspective view of the apparatus 300. The drill guide 12 includes a handle 36 that secures to a drill shaft 38. The handle 36 incorporates an actuatable member 40, shown here in position of the handle 36 for the surgeon to actuate with the thumb. FIG. 10 is an elevation view of the cross-section of the apparatus of FIG. 9 taken at line 10-10. This view shows an example of the integrations of the second portion 358 of the shaft 354 with the body 362 in the first section 368. In one implementation, the body 362 may include a bore (or detent) to receive the second portion 358 under a press and/or interference fit; however, in other configurations, the second portion 358 may secure to the body 362 using appropriately configured welds, fasteners, and like techniques. FIG. 11 is a detail view of the cross-section of FIG. 10. The actuatable member 40 can include a recess 42. Geometry for the recess 42 is compatible with the geometry of the hasp element 388. In use, the surgeon can actuate the actuatable member 40, which moves the recess 42 to secure and release the hasp element 388 on the body.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. An apparatus for indicating the position and length of a bone tunnel, comprising:
   a shaft comprising:
      a first member configured to couple with a drill guide;
      a second member in spaced relation to the first member, the second member comprising an indicator comprising a tube, the tube having a bore extending therethrough, and configured to provide an indication of thickness of a boney member with the first member disposed on a first side of the boney member and the second member disposed on a second side of the boney member;
   a coupling member directly connected at a first end to the first member and directly connected at a second end to the second member;
   a fastening member connected to the first member, the fastening member having a body with a first end and a second end and a bore adapted to receive the drill guide extending between the first and second ends;
   wherein the bore of the fastening member forms a first axis and the bore in the tube forms a second axis that intersects with the first axis at a drill angle;
   wherein the body of the fastening member is tapered from the first end to the second end away from the second axis;
   a planar surface on the second end of the fastening member which is substantially perpendicular to the first axis; and
   an elongated protrusion extending from the planar surface away from the second axis, the elongated protrusion having a diameter smaller than a diameter of the body of the fastening member.

2. The apparatus of claim 1, wherein the coupling member is configured to position the second member on the second side of the boney member with the first member in position on the drill guide.

3. The apparatus of claim 1, wherein the coupling member is a bent portion disposed between the first member and the second member.

4. The apparatus of claim 1, wherein the drill angle is greater than 90 degrees.

5. The apparatus of claim 1, wherein the drill angle is configured to align the second axis with a drill axis on the drill guide with the first member in position on the drill guide.

6. The apparatus of claim 1, wherein the indicator comprises a gauge marker, and wherein the position of the gauge marker relative to the indicator provides the indication of the material thickness of the boney member.

7. The apparatus of claim 6, wherein the indicator comprises a gauge with gauge markings, and wherein the indication corresponds with the position of the gauge marker relative to the gauge markings.

8. The apparatus of claim 1, wherein the elongated protrusion comprises a hasp element configured to couple with the drill guide.

9. The apparatus of claim 1, wherein the bore of the fastening member is a slotted bore configured to receive a portion of the drill guide therein, the slotted bore having an open bottom portion and annular top portion.

10. An apparatus for indicating the position and length of a bone tunnel, comprising:
    a shaft having a first portion and a second portion with a bent portion therebetween;
    wherein a first angle between the first portion and the second portion is greater than 90 degrees;
    a first member coupled with the shaft, the first member comprising a body with a first axis and configured to couple with a drill guide;
    a second member coupled with the shaft, the second member having a bore extending therethrough, the bore forming a second axis;
    wherein the second axis intersects the first axis at a drill angle that is substantially similar to the first angle;
    wherein a second angle between the first portion and the first axis is substantially similar to a third angle between the second portion and the second axis; and
    wherein the shaft is configured to locate the second member in spaced relation to the first member so that the second axis aligns with a drill axis at an end of the drill guide.

11. The apparatus of claim 10, wherein the second portion of the shaft extends in a direction that is parallel to the first axis.

12. The apparatus of claim 10, wherein the first portion of the shaft extends in a direction that is parallel to the second axis.

13. The apparatus of claim 10, further comprising an indicator coupled with the second member, wherein the indicator is configured to provide an indication of thickness of a boney member with the first member disposed on a first side of the boney member and the second member disposed on a second side of the boney member.

14. An apparatus for indicating the position and length of a bone tunnel, comprising:
    a shaft comprising:
        a first member configured to couple with a drill guide;
        a second member in spaced relation to the first member, the second member comprising an indicator comprising a tube, the tube having a bore extending therethrough, and configured to provide an indication of thickness of a boney member with the first member disposed on a first side of the boney member and the second member disposed on a second side of the boney member;
    wherein the first and second members are coupled such that the entire shaft is substantially L-shaped;
    a fastening member connected to the first member, the fastening member having a bore adapted to receive the drill guide;
    wherein the bore of the fastening member forms a first axis and the bore in the tube forms a second axis that intersects with the first axis at a drill angle.

\* \* \* \* \*